United States Patent [19]

Demetrakopoulos

[11] Patent Number: 5,045,058

[45] Date of Patent: Sep. 3, 1991

[54] APPARATUS AND METHOD FOR THE CLEANSING AND ANTISEPSIS OF THE VAGINA

[76] Inventor: George Demetrakopoulos, 1942 Calvert St., NW., Washington, D.C. 20009

[21] Appl. No.: 225,805

[22] Filed: Jul. 29, 1988

[30] Foreign Application Priority Data

Dec. 30, 1987 [GB] United Kingdom ............... 872069

[51] Int. Cl.⁵ .................................. A61M 31/00
[52] U.S. Cl. ................................ 604/55; 604/57; 604/218
[58] Field of Search ............... 604/48, 57, 54, 55, 604/218; 252/174; D28/8.1, 8.2

[56] References Cited

U.S. PATENT DOCUMENTS

| 7,235 | 3/1874 | Burns et al. .............. D28/8.2 |
| 2,900,305 | 8/1959 | Siggia . |
| 3,291,692 | 12/1966 | Hagerty . |
| 3,594,468 | 7/1971 | Saurino . |
| 3,671,545 | 6/1972 | Halpern . |
| 3,840,661 | 10/1974 | Waldstein . |
| 4,309,014 | 1/1982 | Blaszkowski .............. D28/8.1 |
| 4,393,871 | 7/1983 | Vorhauer et al. . |
| 4,839,080 | 6/1989 | Jungermann .............. 252/107 |

OTHER PUBLICATIONS

Syntex Femstat Prefill, Syntex Laboratories, Inc., 12/86.
Gray's Anatomy, Goss, ed., Lea–Febiger (pub.), 1966, pp. 1320 & 1322.

Primary Examiner—Stephen C. Pellegrino
Attorney, Agent, or Firm—Finnegan, Henderson, Farabow, Garrett and Dunner

[57] ABSTRACT

A method and apparatus for the cleansing and antisepsis of the vagina. The apparatus comprises a phallic-shaped solid soap material containing an antiseptic contained in a storage case which also can function as a syringe to rinse the vagina. The method comprises moistening the apparatus until a lather is formed, inserting the apparatus into the vagina, moving the apparatus to deliver lather to appropriate areas of the vagina, withdrawing the apparatus from the vagina and, if necessary, rinsing the vagina.

18 Claims, 2 Drawing Sheets

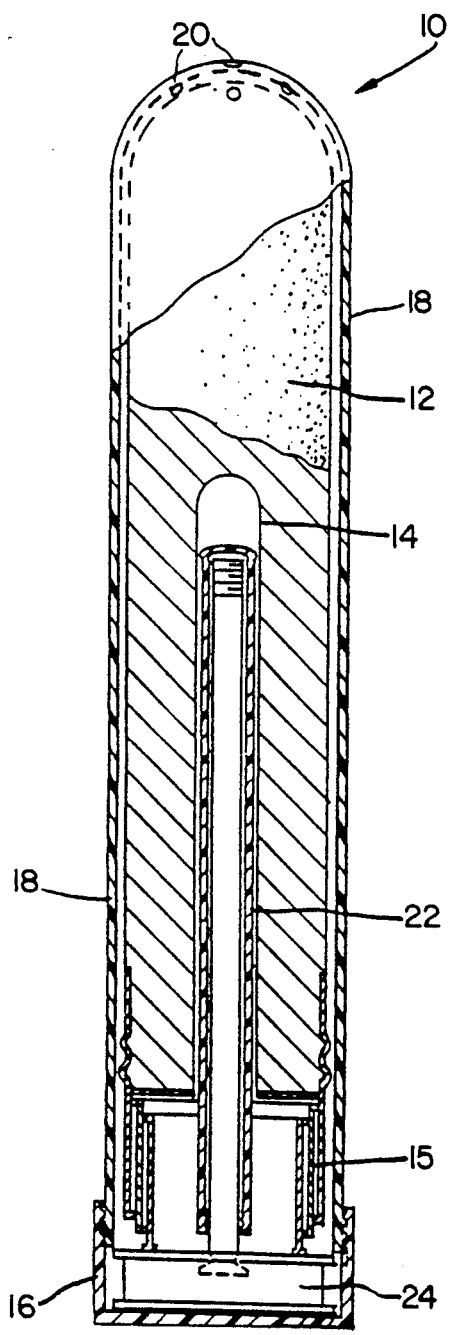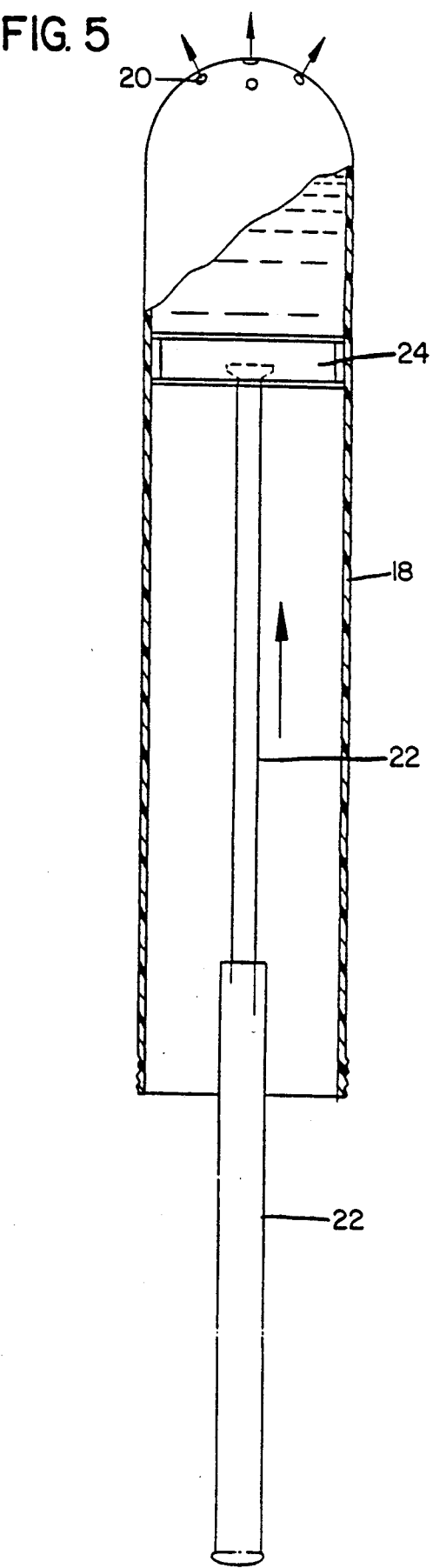

APPARATUS AND METHOD FOR THE CLEANSING AND ANTISEPSIS OF THE VAGINA

BACKGROUND OF THE INVENTION

The present invention relates to an apparatus and method for the cleansing and antisepsis of the vagina.

Currently available means, not requiring a physician, for the treatment of vaginal irritation, itching or infections, and also for regular vaginal hygiene include douching with fluids and inserting suppositories, gels, creams, or ointments into the vagina, either by hand or by vaginal applicators.

Douching is conducted either by utilizing a standard reusable vaginal douche apparatus, which consists of a bag and hook and a long tube and clamp, or by utilizing a single-use, disposable douche consisting of a plastic bottle with a long nozzle.

The technique of douching involves causing a fluid (such as water, pH adjusted water, or water mixed with antiseptics, etc.) to flow in and out of the vagina either by the force of gravity or by pressure. In douching, it is hoped that the fluid will remove unwanted substances such as secretions, bacteria, or yeast, that some of the fluid will remain inside the vagina to achieve a desirable effect such as deodorizing or refreshing, and that certain amounts of the fluid will come into contact with the appropriate areas of the vagina for an effective length of time. The latter is most important in cases where medicated douches are used for treatment of vaginal infections or overgrowth of germs such as yeast, bacteria, molds, chlamydia or viruses. In many cases where a medicated douche is used, not only does the solution have to come into contact with the infected or affected area, but it also must remain in contact with such area for a sufficient period of time to produce the desired results.

Douching with the standard reusable technique utilizing a douche bag and tube is cumbersome because, for douching to be most effective, the user has to lie on a flat surface such as a bathtub or an appropriately covered bed with the pelvis elevated and the bag at an appropriate elevation, and must insert the tube as deeply as possible into the vagina. In utilizing a medicated solution, it is hoped that the solution will, by the force of gravity, reach all of the infected areas and remain in contact with such areas for a sufficient period of time to exert a germicidal effect.

While douching may be an acceptable means for rinsing or deodorizing the vagina, it is not an efficient and effective technique to disinfect the vagina, particularly when medicated solutions are used. This is due to the position of the vaginal canal, its shape and depth, the downward direction of its outer opening, and, in particular, its inner topographic anatomy and physiology. Specifically, difficulties arise because the inner end of the vagina is ring-shaped, with the vaginal dome collapsing against the uterine cervix (anterior and posterior fornix). In addition, the vaginal walls are normally collapsed against each other; and the inner surfaces of the vaginal walls have multiple rugae, villi, folds and creases. In order for douching to be an effective technique, all of these areas have to be stretched adequately for a period of time sufficient to allow the douching fluid to come into contact with them. This becomes even more crucial when medicated solutions are used since the medication not only has to come into contact with the surface where the bacteria or yeast are attached or anchored, but also has to remain there for a sufficient period of time, surviving vaginal secretions, to exert the desired effect.

Utilizing disposable-type douches wherein a nozzle is used to force fluid into the vagina may be less cumbersome, but still suffers from the same disadvantages as those of the standard douching technique. In addition, although the disposable douche technique may produce a more forceful flow of fluid, the flow is limited to the outer part of the vagina because of the size of the nozzle. The nozzle in most cases is not long enough to reach the proximal part of the vagina, i.e., the section towards the cervix. As in standard douches, the fluid reaches the inner part of the vagina only by passive flow, which is inadequate to enable all parts of the vagina to be contacted, particularly at the paracervical dome. Also, the amount of fluid in one disposable douche may not be adequate to distend the vaginal walls and to maintain them in a distended position for a long enough time to expose the vaginal creases and folds to an adequate amount of the medicated fluid. In addition, there is the possibility that the hard nozzle of the disposable douche may cause injury to the vagina.

Because of the above mentioned shortcomings of douching methods, particularly in providing adequate means of hygiene in the proximal part of the vagina and the vulvar area, it is necessary that other antiseptic methods be employed.

Another known method of providing local vaginal hygiene involves the use of vaginal inserts such as tablets, caplets, ointments, creams or gels. These can be inserted into the vagina either by hand or by an applicator. In using such inserts, it is hoped that the inserts eventually will become dispersed and reach all of the affected areas of the inner vagina by melting or mixing with vaginal secretions. These inserts must be delivered by insertion as far as possible into the vaginal tract. Because the tablets are usually too small and the vaginal applicators cannot deliver a large enough dose of medication, it may be necessary to use several doses in an attempt to reach all of the affected areas of the vaginal canal. In addition, in order for the inserts to be most effective, the user has to remain in a horizontal position for a prolonged period of time. Otherwise, a significant portion of the medicated substance will be discharged along with vaginal secretions, particularly when inflamation is present.

Vaginal inserts suffer from the additional disadvantage that residual material such as binders, excipients, etc. and also medication can remain in the vagina and lose their effectiveness after a period of time. This can be caused by body heat, vaginal secretions or pH. Therefore, to achieve vaginal cleansing, the user is often forced to utilize additional douching techniques to remove the remaining materials from the vagina. In the case of gels and ointments that are not water soluble, the residue is often left behind even after douching.

Vaginal inserts also suffer from the same disadvantage as douching techniques in that the shape and configuration of the vagina limits the amount of contact of medication with certain areas of the vagina, particularly at the paracervical dome and the areas covered by downward oriented rugae.

SUMMARY OF THE INVENTION

An object of the present invention is to provide a convenient and effective means for maintaining regular hygiene of the vagina.

Another object of the present invention is to provide an effective means for the prevention and treatment of vaginal infections and irritations.

To achieve the objects in accordance with the purpose of the invention, as embodied and broadly described herein, the present invention provides an apparatus for the cleansing and antisepsis of the vagina comprising a substantially phallic-shaped solid soap material containing an antiseptic. As used herein, the term antiseptic includes those substances that kill germs or prevent or slow the growth of germs.

As embodied and broadly described herein, the present invention also provides a method for the cleansing and antisepsis of the vagina utilizing the above apparatus comprising moistening the apparatus until a lather is formed, inserting the apparatus into the vagina, moving the apparatus to deliver lather to the appropriate areas of the vagina and withdrawing the apparatus from the vagina.

The accompanying drawings, which are incorporated in and constitute a part of this specification, illustrate the invention and preferred embodiments of the invention and, taken together with the description, serve to explain the principles of the invention.

BRIEF DESCRIPTION OF THE DRAWINGS

FIG. 1 is a diagram of one embodiment of the apparatus of the present invention illustrating a solid soap material having a hollow inner core for housing a telescoping plunger, all enclosed within an outer casing.

FIG. 5 is a diagram of the telescoping plunger and outer cap which is capable of being utilized as a syringe for washing the vagina.

DETAILED DESCRIPTION OF PREFERRED EMBODIMENTS

Figure 2:
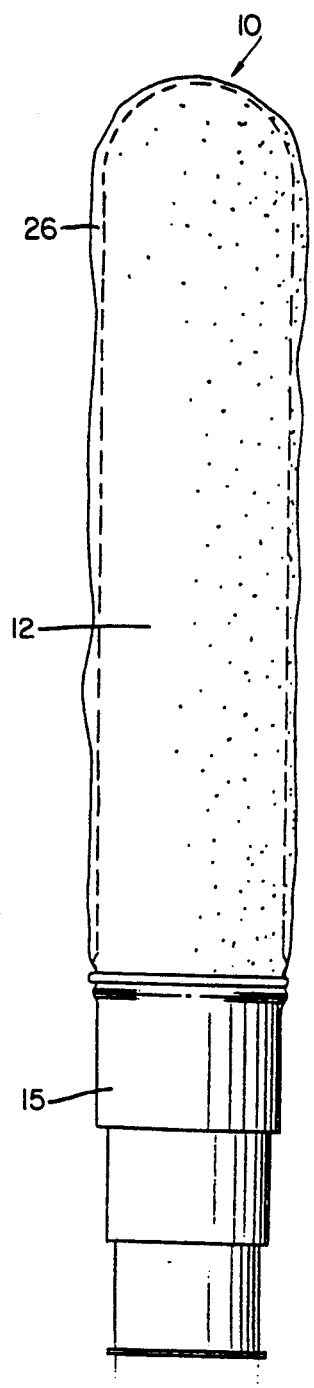
FIG. 2 is a diagram of the embodiment of the invention illustrated in FIG. 1, further including a porous sheath material surrounding the solid soap material and also including a telescoping handle.

Reference will now be made in detail to the present preferred embodiments of the invention, examples of which are illustrated in the accompanying drawings.

In accordance with the present invention and as illustrated by FIG. 1, an apparatus 10 for the cleansing and antisepsis of the vagina comprises a phallic-shaped solid soap material 12 containing an antiseptic. The term phallic-shaped as used herein means substantially cylindrical, and having a rounded end. This shape allows solid soap material 12 to come into contact with hard to reach areas of the vagina, such as the paracervical dome. The length of solid soap material 12 of the present invention preferably ranges from 4 to 10 inches and the diameter preferably ranges between $\frac{1}{2}$ and $2\frac{1}{2}$ inches.

The antiseptic contained in solid soap material 12 is preferably povidone-iodine and is preferably present in a concentration ranging from 0.025 to 5.0% by weight. Povidone-iodine is a 1-vinyl-2-pyrrolidinone polymer with iodine, having the formula $(C_6H_9ON)_nI$ and is a well known antiseptic. Solid soap material 12 may also contain other additives such as vitamin E, petroleum jelly, lecithin, cocoa butter, deodorants, perfumes, colorants, etc.

In accordance with the invention as illustrated in FIG. 1, solid soap material 12 includes a hollow core 14, substantially cylindrical and preferably made of plastic or hard rubber. Hollow core 14 of solid soap material 12 is attached to handle 15. Hollow core 14 provides support and reinforcement for solid soap material 12. The apparatus 10 further includes an outer casing preferably made of a plastic material and comprised of an end cap 16 and a main casing 18. Main casing 18 and end cap 16 attach to each other to function as a carrying case for solid soap material 12. Main casing 18 preferably has the same overall shape as solid soap material 12, i.e., a phallic shape. The rounded end of main casing 18 contains a plurality of openings 20. Hollow core 14 contains a telescoping plunger 22 which is attached to a rubber head 24, both of which can be enclosed inside the outer casing for storage of apparatus 10. A telescoping handle 15 is attached to the base of solid soap material 12. Rubber head 24 is made of a deformable rubber material and is sized so that it can fit inside and slide within main casing 18.

In accordance with the invention as illustrated in FIG. 2, solid soap material 12 may be surrounded by a porous sheath 26. Porous sheath 26 may be a stocking-like material or a sponge-like material, or any material which will allow the passage of lather from solid soap material 12 but will prevent the escape of solid material. Therefore, during use of the apparatus 10, solid pieces of soap material are prevented from entering the vagina. Porous sheath 26 may be attached at the base of solid soap material 12 and may be stored inside the outer casing.

The apparatus 10 may also include a telescoping handle 15 which can be extended to increase its overall length to allow the user to conveniently grasp apparatus 10. Telescoping handle 15 can be retracted to a minimum length to allow apparatus 10 to be contained in the outer casing (as shown in FIG. 1).

Figure 3:
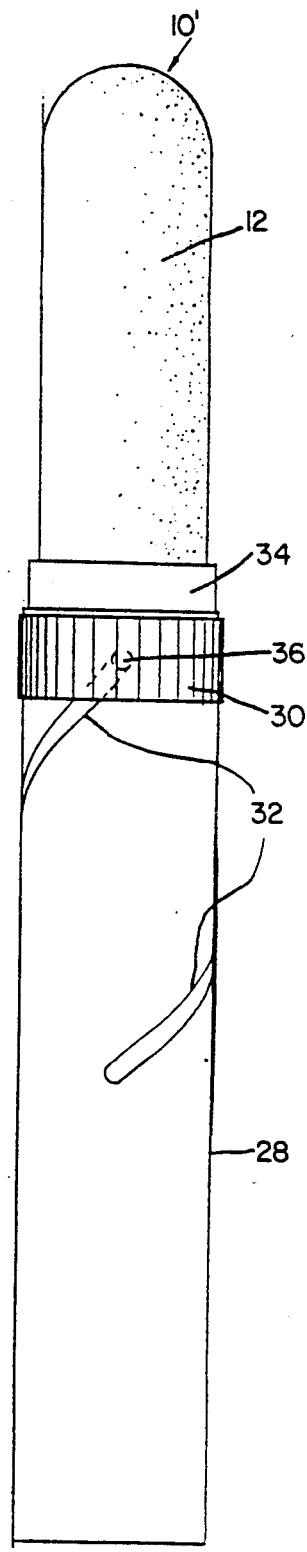
FIG. 3 is a diagram of a second embodiment of the apparatus of the present invention illustrating a housing including a rotatable member capable of causing the solid soap material to extend out of and retract into the housing.

In accordance with another embodiment of the invention as illustrated in FIG. 3, solid soap material 12 may be contained within a housing 28. In this embodiment, apparatus 10' includes a rotatable member 30 for causing solid soap material 12 to extend from or retract into housing 28. A helical groove 32 is located within housing 28. Rotatable member 30 is attached to a collar 34 which is attached to solid soap material 12. A pin 36 is fitted within helical groove 32 and is attached to rotatable member 30. As rotatable member 30 is rotated, pin 36 tracks within helical groove 32 which forces rotatable member 30, collar 34 and ultimately solid soap material 12 to move out of or into housing 28. Therefore, by rotating rotatable member 30, solid soap material 12 can be extended out of, and retracted into housing 28, allowing apparatus 10' to function similar to a lipstick-like device. A variety of other apparatuses for causing solid soap material 12 to extend from and retract into housing 28 would be known by those skilled in the art and are within the scope of the present invention.

Figure 4:
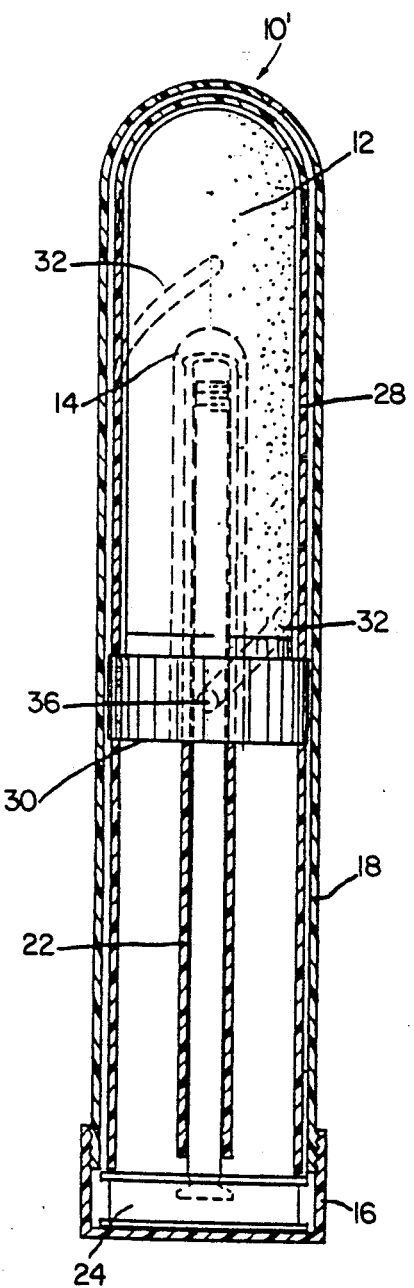
FIG. 4 is a diagram of the apparatus of FIG. 3 in the retracted position and contained within an outer casing.

In accordance with the invention as illustrated in FIG. 4, apparatus 10' of FIG. 3 may be contained within an outer casing comprised of main casing 18 and end cap 16 as in the embodiment illustrated in FIG. 1. Solid soap material 12 may also contain hollow core 14 which houses telescoping plunger 22.

The apparatus of the present invention can be utilized in a method for the cleansing and antisepsis of the vagina. Main casing 18 and end cap 16 are first detached from one another and removed prior to use of the apparatus in the method of the present invention. Solid soap material 12 can be grasped by the user by means of handle 15. The method comprises the steps of moistening solid soap material 12 to cause the formation of a soap lather, inserting solid soap material 12 into the vagina, moving the apparatus to contact the appropriate areas of the vagina, and then withdrawing solid soap material 12 from the vagina. The procedure may be repeated until sufficient foam has been delivered to appropriate areas of the vagina. The soap lather can either be left inside the vagina or may be removed by washing, preferably after waiting a period of at least 3 minutes.

The apparatus of the present invention may be utilized for washing the vagina a illustrated in FIG. 5. Rubber head 24 is inserted into main casing 18. Rubber head 24 is made of a material which allows it to sealably fit inside and slide within main casing 18. Telescoping plunger 22 is then extended to its maximum length. When extended, telescopic plunger 22 is approximately twice as long as when retracted. The entire apparatus consisting of telescoping plunger 22 and main casing 18 can now be utilized as a syringe. Main casing 18 and be inserted into a fluid such as water and the fluid can be drawn into main casing 18 through openings 20 by pulling out telescoping plunger 22. Main casing 18 can then be inserted into the vagina and the water or other fluid injected through openings 20 by pushing telescoping plunger 22 in. This procedure can be repeated until the vagina has been adequately flushed. Upon completion, telescoping plunger 22 can then be conveniently replaced within hollow core 14 and end cap 16 can be reattached to main casing 18 to enclose the entire apparatus, including solid soap material 12.

The apparatus and method of the present invention allows for easy cleansing and antisepsis of the vagina while avoiding the cumbersome and inconvenient procedure of douching. The user may use the apparatus and method of the present invention in an office, while traveling, or any place where water is available. The user does not have to undress to the extent required for douching because the medicated lather can be delivered with only a small amount of fluid. The method and apparatus can be utilized even with the user in an upright position because the method does not require the force of gravity as does douching. Because of the shape, consistency and composition of the apparatus of the present invention, the user has direct control of the application and distribution of the soap lather and medication. The apparatus and method overcome the limitations of douching in that the user can stretch the vagina walls and can even sequentially stretch particular parts of the vagina while at the same time applying soap and medication to these parts. This stretching of the vagina may also allow for the draining of undesirable vaginal secretions from between inflamed rugae or folds. The present apparatus and method are also effective for the cleansing and antisepsis of the vulvar and perineal areas of the vagina, unlike the method of douching.

It will be apparent to those skilled in the art that various modifications and variations can be made in the apparatus and method of the present invention without departing from the scope or spirit of the invention. Thus, it is intended that the present invention covers the modifications and variations of this invention provided they fall within the scope of the appended claims and their equivalents.

What is claimed is:

1. An apparatus for use in cleansing and antisepticizing the vagina, comprising a substantially phallic-shaped solid soap material containing an antiseptic. a substantially cylindrical reinforcing non-soap core material embedded within said solid soap material, a substantially phallic-shaped removable outer casing disposed around and completely enclosing said solid soap material, a telescoping plunger disposed to fit inside said core material and a rubber head attached to said plunger at one end, wherein said rubber head is disposed to slidably engage inside said main casing, thereby enabling said telescoping plunger, said rubber head. and said main casing to function as a syringe.

2. The solid soap material of claim 1. wherein said antiseptic is povidone-iodine.

3. The solid soap material of claim 1. wherein said povidone-iodine is present in said solid soap material in a concentration ranging from 0.025 to 5.0%, by weight.

4. The solid soap material of claim 1, wherein said solid soap material has an overall length ranging from 4 to 10 inches and a diameter ranging from ½ to 2½ inches.

5. The solid soap material of claim 1. wherein said core material is plastic.

6. The solid soap material of claim 1. wherein said core material is rubber.

7. The solid soap material of claim 1, wherein said core material is hollow.

8. The solid soap material of claim 1, wherein said outer casing comprises a main casing and an end cap adapted to be coupled to said main casing, said main casing having a substantially phallic shape with a rounded end and including a plurality of apertures in the rounded end.

9. The solid soap material of claim 8, wherein said outer casing is plastic.

10. The apparatus of claim 1, where solid soap material, said rubber head and said telescoping are enclosed within said outer casing.

11. The solid soap material of claim 10, further comprising an expandable porous sheath attached at the base of said solid soap material and disposed around said solid soap material.

12. The solid soap material of claim 4, wherein said porous sheath is a sponge.

13. The solid soap material of claim 4, wherein said porous sheath is a stocking.

14. The solid soap material of claim 4, further comprising a handle attached to the base of said solid soap material.

15. The solid soap material of claim 14, wherein said handle is telescopic.

16. The solid soap material of claim 10. wherein said solid soap material is enclosed within a housing.

17. The solid soap material of claim 16, further comprising a rotatable member for extending and retracting said solid soap material from said housing.

18. A method for the cleansing and antisepsis of the vagina utilizing a substantially phallic-shaped solid soap material containing an antiseptic; said solid soap material including a hollow substantially cylindrical reinforcing non-soap core material embedded therein; a substantially phallic-shaped removable outer casing including a main casing with a substantially phallic shape and a plurality of apertures and an end cap adapted to be coupled to said main casing; and a telescoping plunger enclosed within said outer casing and disposed to fit inside the hollow core material, one end of the telescoping plunger attached to a rubber head disposed to slidably engage inside the main casing; said method comprising the steps of removing said end cap from said main casing, removing said telescoping plunger from said hollow core, moistening the solid soap material until a lather is formed, inserting the solid soap material into the vagina, moving the solid soap material to deliver lather to appropriate areas of the vagina, withdrawing the solid soap material from the vagina, inserting said rubber head into said main casing to form a syringe-like device, extending said telescoping plunger, drawing a fluid into said main casing, inserting said main casing into the vagina and discharging the fluid into the vagina to remove said lather.

* * * * *

UNITED STATES PATENT AND TRADEMARK OFFICE
CERTIFICATE OF CORRECTION

PATENT NO. : 5,045,058

DATED : September 3, 1991

INVENTOR(S) : GEORGE DEMETRAKOPOULOS

It is certified that error appears in the above-identified patent and that said Letters Patent is hereby corrected as shown below:

On the title page, item [30] Foreign Application Priority Data, change "United Kingdom" to --Greece--.

Claim 3, column 6, line 25, change "claim 1" to --claim 2--.

Claim 10, column 6, line 45, change "where" to --wherein said--.

column 6, line 46, after "telescoping" insert --plunger--.

Claim 12, column 6, line 52, change "claim 4" to --claim 11--.

Claim 13, column 6, line 54, change "claim 4" to --claim 11--.

Claim 14, column 6, line 56, change "claim 4" to --claim 11--.

Signed and Sealed this

Twentieth Day of October, 1992

Attest:

DOUGLAS B. COMER

*Attesting Officer*      *Acting Commissioner of Patents and Trademarks*